United States Patent
Moore et al.

(10) Patent No.: US 9,683,460 B2
(45) Date of Patent: Jun. 20, 2017

(54) SYSTEM AND METHOD FOR INSPECTING TURBOMACHINES

(71) Applicant: General Electric Company, Schenectady, NY (US)

(72) Inventors: Lawrence James Moore, Clifton Park, NY (US); Fredrick Levi Fuller, Schenectady, NY (US); Jason Michael Boss, Glenville, NY (US); Bernard Baran Zabek, Clifton Park, NY (US); Gerald Marco Geraci, Rochester, NY (US); Michael Richard Pomykai, Scotia, NY (US)

(73) Assignee: General Electric Company, Schenectady, NY (US)

( * ) Notice: Subject to any disclaimer, the term of this patent is extended or adjusted under 35 U.S.C. 154(b) by 319 days.

(21) Appl. No.: 14/588,173

(22) Filed: Dec. 31, 2014

(65) Prior Publication Data

US 2016/0010505 A1 Jan. 14, 2016

Related U.S. Application Data

(60) Provisional application No. 62/023,367, filed on Jul. 11, 2014.

(51) Int. Cl.

| F01D 25/28 | (2006.01) |
|---|---|
| F01D 21/00 | (2006.01) |
| G01L 9/00 | (2006.01) |
| G01N 25/00 | (2006.01) |
| G01M 15/14 | (2006.01) |
| G01N 21/954 | (2006.01) |

(Continued)

(52) U.S. Cl.
CPC ......... *F01D 25/285* (2013.01); *F01D 21/003* (2013.01); *G01L 9/00* (2013.01); *G01M 15/14* (2013.01); *G01N 21/954* (2013.01); *G01N 25/00* (2013.01); *B23Q 3/1554* (2013.01); *B64D 47/08* (2013.01); *F05D 2260/80* (2013.01); *F05D 2260/83* (2013.01); *G01N 2021/9542* (2013.01); *G05B 2219/40607* (2013.01); *Y10S 901/44* (2013.01)

(58) Field of Classification Search
CPC .......................... F01D 25/285; G02B 23/2492
See application file for complete search history.

(56) References Cited

U.S. PATENT DOCUMENTS

| 4,063,228 A | 12/1977 | Eggenberger et al. |
| 4,392,344 A * | 7/1983 | Gordon .................. F16G 13/16 138/120 |

(Continued)

*Primary Examiner* — Peter Macchiarolo
*Assistant Examiner* — Timothy Graves
(74) *Attorney, Agent, or Firm* — James W. Pemrick; Ernest G. Cusick; Frank A. Landgraff

(57) ABSTRACT

A method for inspecting a turbomachine is provided. The method includes the steps of, attaching a gimbal mount to the turbomachine, inserting a probe into the turbomachine through the gimbal mount, and adjusting a position of the probe via the gimbal mount. A removing step removes the probe from the turbomachine. An attaching step attaches a traverse actuator system to the gimbal mount. The traverse actuator system is connected to the gimbal mount through a pressure isolation system. A reinserting step is used to reinsert the probe back into the turbomachine. An inspecting step is used to inspect or test the turbomachine.

32 Claims, 8 Drawing Sheets

(51) Int. Cl.
*B23Q 3/155* (2006.01)
*B64D 47/08* (2006.01)

(56) References Cited

U.S. PATENT DOCUMENTS

| | | | | |
|---|---|---|---|---|
| 4,732,526 | A * | 3/1988 | Nakashima | B25J 9/046 |
| | | | | 310/88 |
| 5,383,355 | A * | 1/1995 | Baleras | G01M 15/00 |
| | | | | 73/112.01 |
| 7,789,356 | B1 * | 9/2010 | Jones | F16M 11/16 |
| | | | | 248/178.1 |
| 8,045,144 | B2 | 10/2011 | Manfred | |
| 2004/0068232 | A1 * | 4/2004 | Hart | A61B 17/3462 |
| | | | | 604/167.06 |
| 2007/0115116 | A1 | 5/2007 | Zabek | |
| 2009/0027665 | A1 * | 1/2009 | Ogburn | G02B 23/2484 |
| | | | | 356/241.1 |
| 2009/0262354 | A1 * | 10/2009 | Horiuchi | G01N 21/954 |
| | | | | 356/445 |
| 2013/0168971 | A1 | 7/2013 | Maddaus | |
| 2013/0240054 | A1 | 9/2013 | Fuller et al. | |
| 2014/0156073 | A1 * | 6/2014 | Zhang | B25J 9/1689 |
| | | | | 700/257 |

* cited by examiner

US 9,683,460 B2

SYSTEM AND METHOD FOR INSPECTING TURBOMACHINES

BACKGROUND OF THE INVENTION

The subject matter disclosed herein relates to turbomachine inspection and/or testing. More particularly, the subject matter relates to a system and method for inspecting and/or testing operating turbomachines.

In a turbine system, such as a steam turbine system, fluid flow is directed to selected portions of the turbine system to enable production of mechanical energy. Parameters relating to the fluid flow in the system may be measured to evaluate efficiency and performance for a particular turbine design. For example, pressure may be tested at selected locations in the turbine system using pressure tap assemblies. In certain locations, space for installation of the pressure tap assembly is reduced, causing difficulties when attempting to properly seal the assembly in the component. Fluid leaks at the pressure tap assembly proximate the main flow path can disrupt fluid flow, lead to measurement errors and reduce the accuracy of turbine efficiency calculations. Pressure tap assemblies are fixed and are limited to readings at a single location. Therefore, samples are difficult, if not impossible, to obtain from multiple locations in the operating steam turbine.

BRIEF DESCRIPTION OF THE INVENTION

In an aspect of the present invention, a method for inspecting a turbomachine is provided. The method includes the steps of, attaching a gimbal mount to the turbomachine, inserting a probe into the turbomachine through the gimbal mount, and adjusting a position of the probe via the gimbal mount. A removing step removes the probe from the turbomachine. An attaching step attaches a traverse actuator system to the gimbal mount. The traverse actuator system is connected to the gimbal mount through a pressure isolation system. A reinserting step is used to reinsert the probe back into the turbomachine. An inspecting step is used to inspect or test the turbomachine.

In another aspect of the present invention, a method for inspecting an operating turbomachine is provided. The method includes the step of attaching a gimbal mount to the turbomachine. The gimbal mount includes a plurality of turnbuckles located at equal intervals around the gimbal mount, and the gimbal mount is configured to be mounted to a port or a vessel flange of the turbomachine. Adjustment of the turnbuckles translates into a tangential or axial adjustment of a sensor head position for the probe. An inserting step inserts a probe into the turbomachine through the gimbal mount. An adjusting step adjusts a position of the probe via the gimbal mount. A removing step removes the probe from the turbomachine. An attaching step attaches a traverse actuator system to the gimbal mount. The traverse actuator system is connected to the gimbal mount through a pressure isolation system. A connecting step connects a mounting plate to a complementary mounting plate. The mounting plate is attached to a rail, and the rail supports both the pressure isolation system and the gimbal mount. The mounting plate is configured to align with the complementary mounting plate connected to the traverse actuator system, and a plurality of keys are interposed between the mounting plate and the complementary mounting plate to ensure alignment between the traverse actuator system and the gimbal mount. A reinserting step reinserts the probe back into the turbomachine. An inspecting step inspects and/or tests the turbomachine, and a reading step reads at least one of pressure values, temperature values or moisture values obtained from within the operating turbomachine.

DETAILED DESCRIPTION OF THE INVENTION

One or more specific aspects/embodiments of the present invention will be described below. In an effort to provide a concise description of these aspects/embodiments, all features of an actual implementation may not be described in the specification. It should be appreciated that in the development of any such actual implementation, as in any engineering or design project, numerous implementation-specific decisions must be made to achieve the developers' specific goals, such as compliance with machine-related, system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "one aspect" or "an embodiment" or "an aspect" of the present invention are not intended to be interpreted as excluding the existence of additional embodiments or aspects that also incorporate the recited features.

Figure 1:
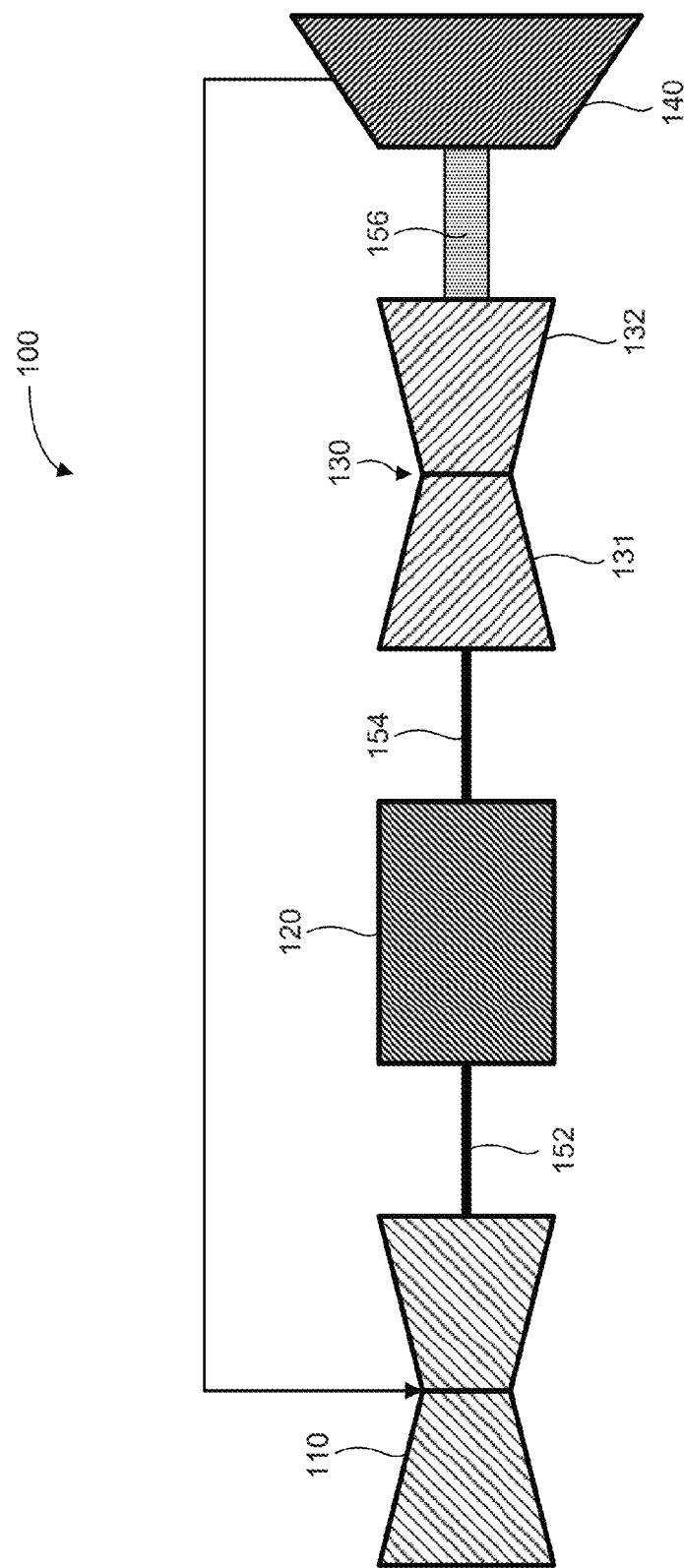
FIG. 1 is a simplified schematic illustration of a combined cycle power plant.

FIG. 1 is a simplified schematic illustration of a combined cycle power plant 100. The power plant 100 includes a steam turbine 110, a generator 120 a gas turbine 130 and a heat recovery steam generator (HRSG) 140. The steam turbine 110 is connected to the generator via shaft 152 and a clutch (not shown). The generator is connected to the gas turbine via shaft 154. The exhaust of gas turbine 130 is connected to HSRG 140 via duct 156, or in some applications the HSRG 140 may either be directly connected to the exhaust of turbine 130 or connected to the exhaust through a diffuser (not shown). The steam turbine 110 converts the thermal energy in steam to rotational movement. Steam strikes the blades of the steam turbine, causing the steam turbine rotor shaft to rotate. The rotating shaft drives the generator 120. The gas turbine 130, which includes a compressor 131 and a turbine section 132, compresses air and mixes it with fuel. The fuel is burned and the hot air-fuel mixture is expanded through the gas turbine blades, making them spin. The spinning gas turbine shaft drives the generator 120, which converts the spinning energy into electricity. The HSRG 140 turns the gas turbine exhaust heat into steam, and this steam is then fed into steam turbine 110.

The steam turbine 110, compressor 131 and gas turbine 132 are all turbomachines. Turbomachines may include multiple stages of blades, buckets, nozzles and vanes. The blades and buckets are rotating elements including airfoil sections. The airfoil sections are designed for high efficiency. At times, it is desirable to inspect and/or test the operation of turbomachines to either (1) validate predicted operating parameters and conditions, or (2) identify problem locations or components, or operating conditions causing undesired characteristics. In some cases, it may be helpful to monitor pressure or temperature along multiple radial distances near a blade. For example, one reading could be taken near the rotor shaft, a second reading near a blade tip and a third reading near the middle of the blade. In the past this has been very difficult, if not impossible, because one could not easily, safely and accurately move a probe in an operating turbomachine. The turbomachine has to be operating for accurate operating measurements. Unfortunately, the blades rotate circumferentially at high speeds and the machines may be under vacuum or pressure, and this makes moving a probe and maintaining the machine seals problematic.

Figure 2:
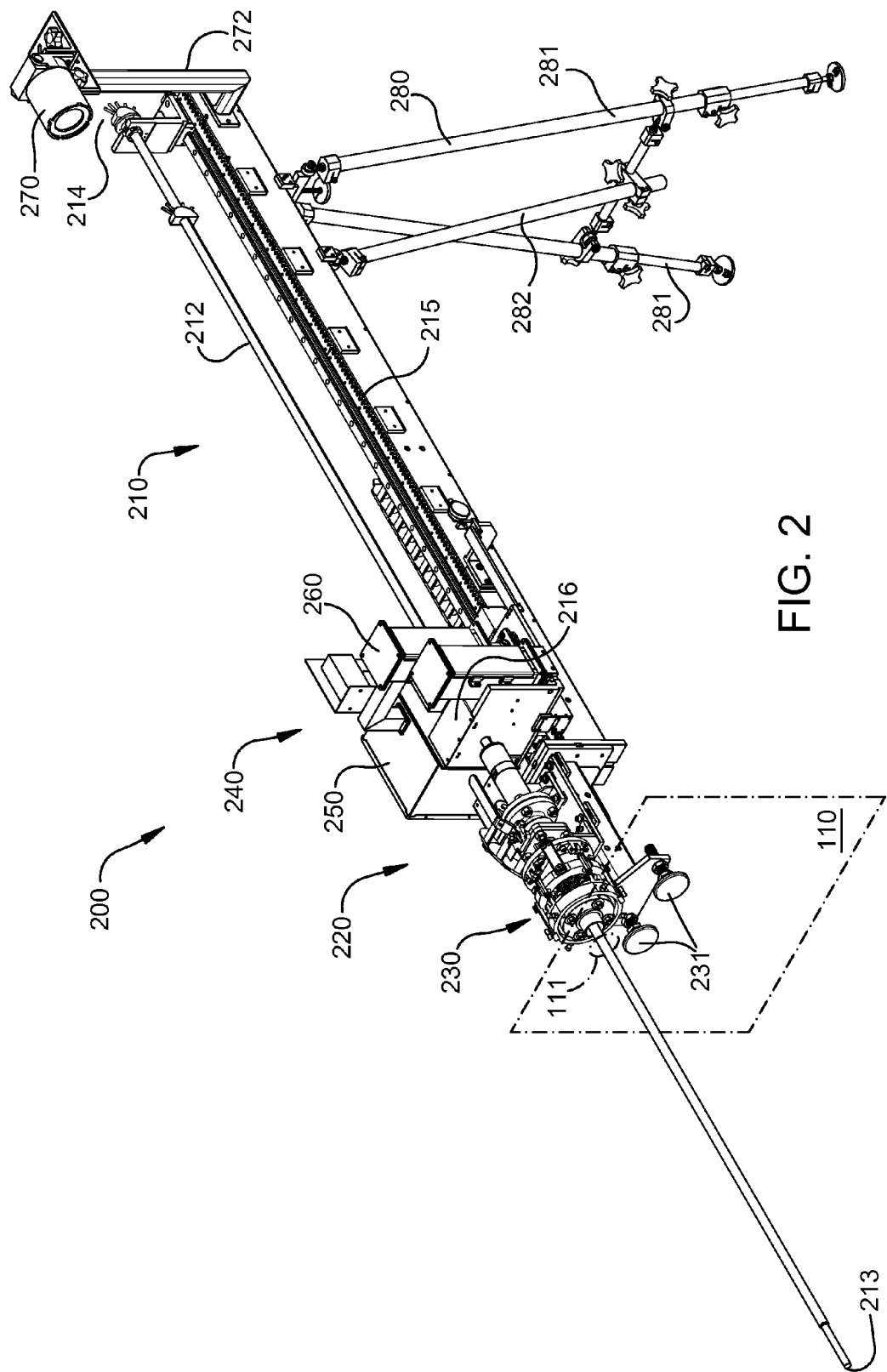
FIG. 2 illustrates a perspective view of a system for inspecting a turbomachine, according to an aspect of the present invention.
Figure 3:
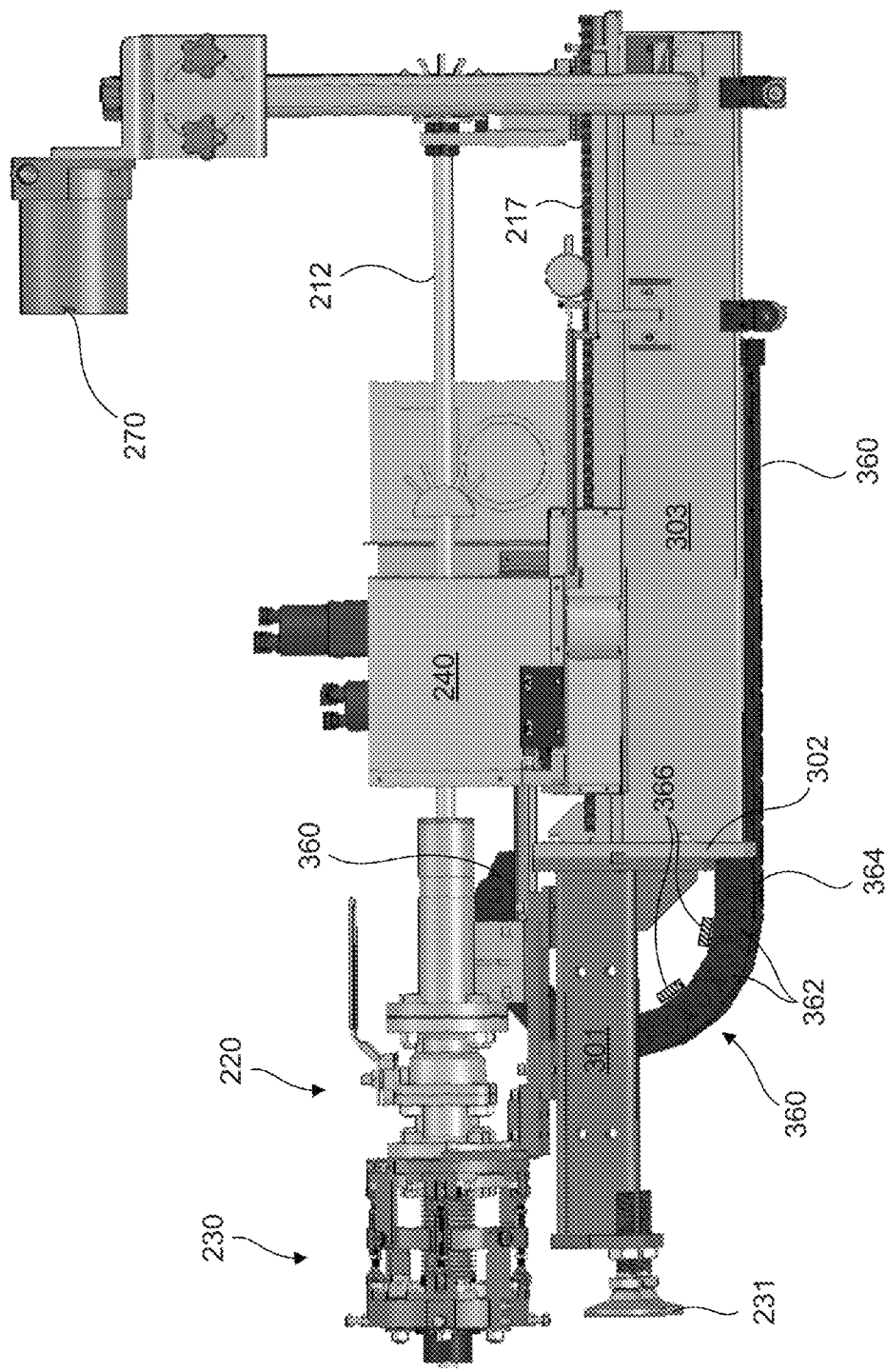
FIG. 3 illustrates a side view of a system for inspecting a turbomachine, according to an aspect of the present invention.

FIG. 2 illustrates a perspective view of a system 200 for inspecting a turbomachine, and FIG. 3 illustrates a side view of a system for inspecting a turbomachine, according to an aspect of the present invention. The system 200 includes a traverse actuator system 210, pressure isolation system 220 and a gimbal mount 230. The pressure isolation system 220 is connected to the traverse actuator 210, and is configured to maintain a pressure resistant seal around the probe 212. The gimbal mount 230 is connected to the pressure isolation system 220. The probe 212 may be formed of an elongated shaft with a sensor head 213 at one end and a plurality of output ports 214 located at an opposing end of the shaft. As one example, the sensor head 213 may be a S-port pressure sensor, and accordingly there would be five output ports 214 at an opposing end of the elongated shaft. Alternatively, the sensor head 213 could be a temperature sensor, a moisture or humidity sensor, or a camera or any other desired sensor device. The elongated shaft of probe 212 is sized for the specific turbine or turbomachine. Any suitable length may be employed, as long as the probe can travel the desired distance into the turbomachine.

The system 200 is configured to mount onto the outer shell or casing of the turbomachine, so that the probe 212 will be aligned to an access port therein. In the example shown, the system 200 is mounted to the steam turbine's 110 casing. An access port 111 is located in the casing of the steam turbine and the probe 212 passes through this opening. The gimbal mount 230 may be fastened to the port 111 by mechanical fasteners, clamps or any other suitable attachment means. A pair of leveling feet 231 may be used to balance and steady the system against the casing of the steam turbine 110.

The traverse actuator 210 includes a carriage 240 configured to move the probe 212 in a linear or radial direction (with respect to the turbomachine) into and out of the turbomachine. A track 215 has a plurality of linearly arranged teeth 217 configured for operation with the carriage 240. The teeth may be located on one or both sides of the track. A motor 260 is operably connected with the carriage 240 and track 215, and is configured to engage the teeth of the track so that operation of the motor forces the carriage to move along the track. For example, the motor may be connected to a gearbox and/or a roller pinion that engages the track teeth. When the roller pinion is rotated by the motor, the carriage 240 moves along the track 215, and the probe moves toward or away from the steam turbine 110. As FIG. 2 illustrates, the carriage 240 is at its most forward position indicating that the probe is at the deepest position within steam turbine 110. The motor can be energized to move carriage back along track 215 to withdraw the probe's sensor head 213.

The traverse actuator 210 also includes an enclosure 250 that is configured to operate in hazardous environments. For example, a hydrogen exclusion zone could be considered a hazardous environment, or any turbomachine that operates under a pressure or vacuum may present hazardous conditions. The enclosure 250 may contain motor 260, sensors for reading the outputs 214 of probe 212, and/or any other desired inspection equipment. The traverse actuator may also include a yaw drive 216 configured to rotate the probe about the radial axis. The yaw drive can include a motor and one or more rollers that engage the probe 212. If the sensor head 213 needs to be rotated, then the yaw drive can adjust the rotational position of the sensor head 213 (e.g., by about +/−180 degrees, +/−150 degrees, etc.). A camera 270 is mounted to the traverse actuator and is configured to observe an insertion location of the probe 212. The camera 270 is ruggedized and configured to operate in hazardous environments (e.g., it can be explosion resistant). The camera enables an operator to remotely view the system 200 and the insertion location of steam turbine 110, from a safe and secure location. The camera can be mounted on an extending arm 272 for an elevated worksite view. In addition, the camera 270 can be connected to the remote monitoring station (that has a display) via a wired or wireless link. The camera can be configured to pan or zoom to a specific field of view, all under remote control.

A leg assembly 280 (e.g., a bipod, tripod, etc.) may also be attached to traverse actuator 210 to stabilize and secure the system. The leg assembly 280 includes a plurality of adjustable length legs configured to lock in position at a desired length. For example, two main legs 281 may be telescopic and have fasteners (e.g., bolts) to lock each leg at a desired length. A third leg 282 may slide within a clamp that also locks the third leg in a desired position and length (e.g., via a clamp). The traverse actuator 210 may also include an articulated cable guide 360 comprised of a plurality of chain links 362. The articulated cable guide 360 retains a plurality of cables that may extend between the output ports 214 and the enclosure 250. The cable guide 360 is comprised of two spaced but parallel chain link walls 362, and a segmented floor 364. The cables reside between the walls 362 and may be retained by top members 366. The cable guide 360 follows (e.g., bends and flexes with) the movement of the carriage 240 so that the cables avoid catching on obstructions as the carriage moves back and forth along rail 303.

Figure 4:
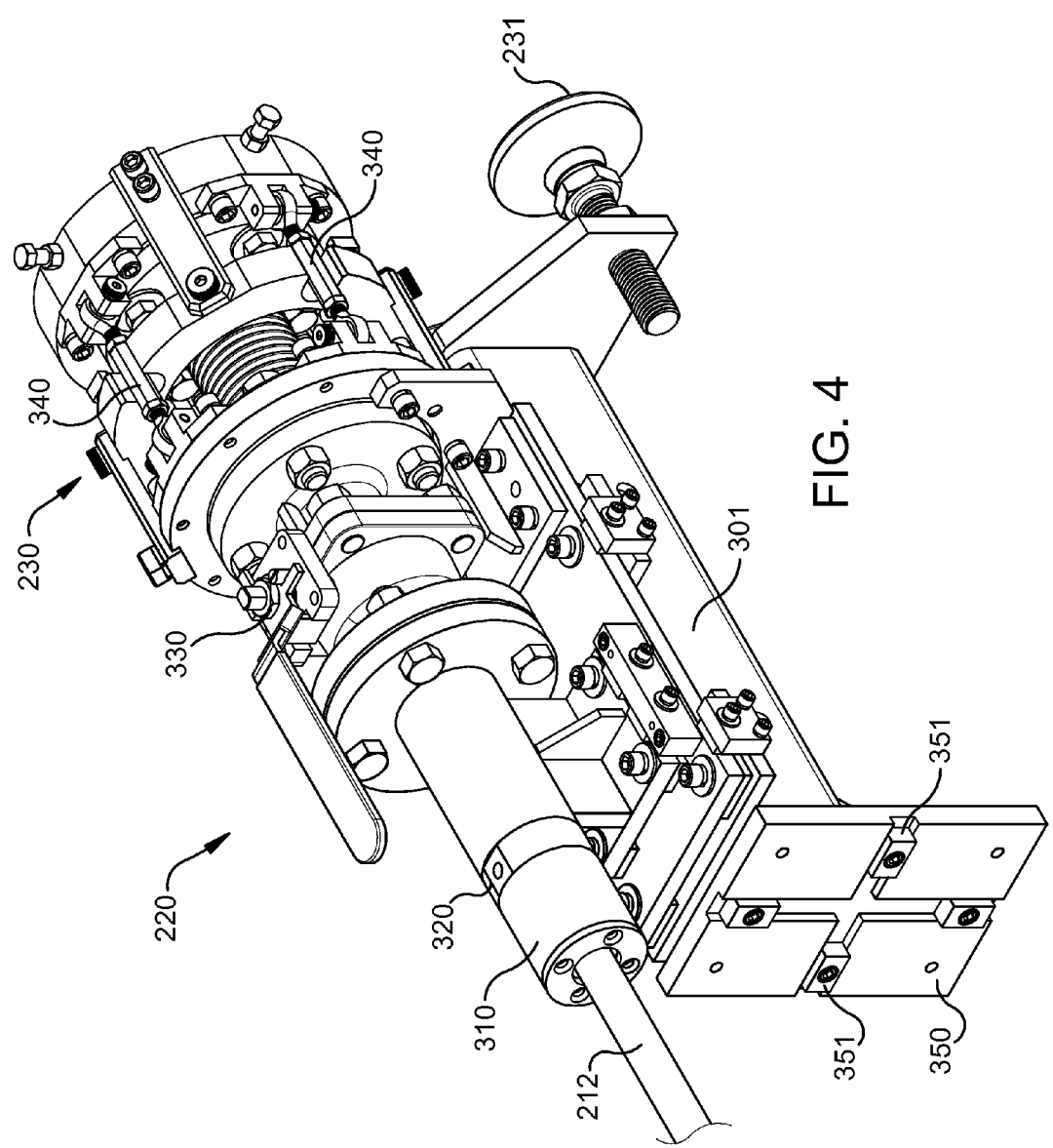
FIG. 4 illustrates a perspective view of the pressure isolation system and the gimbal mount, according to an aspect of the present invention.

FIG. 4 illustrates a perspective view of the pressure isolation system 220 and gimbal mount 230, according to an aspect of the present invention. FIG. 4 illustrates a cross-sectional view of the pressure isolation system 220 and gimbal mount 230, according to an aspect of the present invention. The pressure isolation system 220 is mounted onto rail 301, which in turn is connected to leveling feet 231 (only one of which is shown). The probe 212 is shown inserted into the pressure isolation system. A probe bearing 310 facilitates movement of the probe 212, and the bearing 310 could be comprised of roller bearings, ball bearings or any other suitable low friction device or material. For example, as the probe 212 is moved back and forth (or along a radial axis of the turbomachine) the bearing 310 reduces friction between the probe 210 and the surrounding components of the system. A pressure seal block 320 isolates the pressure within the turbomachine from the external atmosphere, and seals along the outer circumference of probe 212. The pressure seal block 320 may be connected to a pressurized or vacuum source. For example, if the turbomachine location undergoing inspection is at 10 psi, the seal block could be maintained at about 15 psi to prevent undesired leakage.

A valve seal 330 is located between the gimbal mount 230 and the pressure seal block 320. The valve seal 330 is configured to isolate the pressure seal block 320 from the gimbal mount 230 when the probe is not in the valve seal. In addition, the valve seal 330 can be closed to isolate the internal working area of the turbomachine from the external atmosphere. The valve seal may be a ball valve seal (as shown), a guillotine seal or any other suitable seal.

Figure 5:
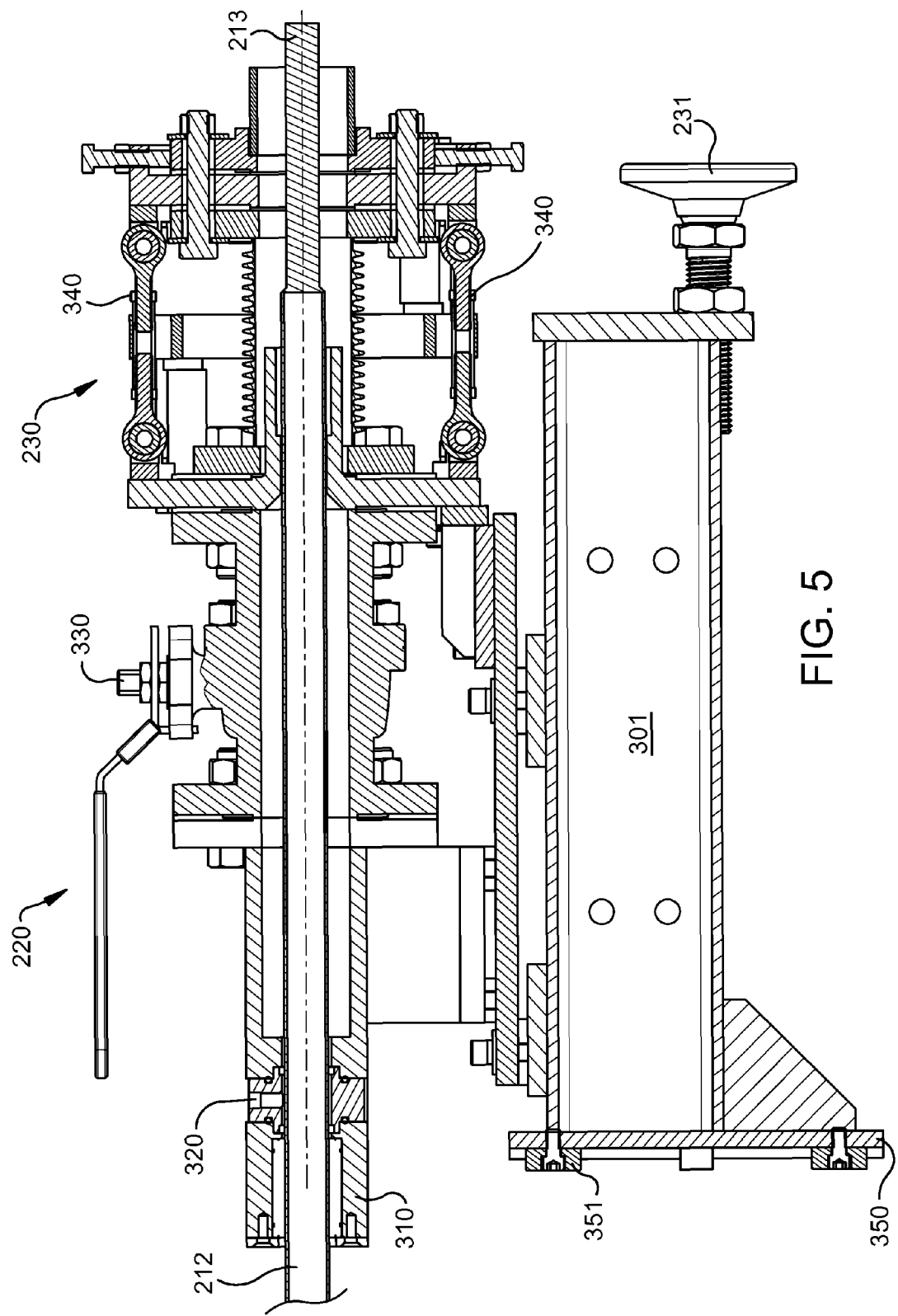
FIG. 5 illustrates a cross-sectional view of the pressure isolation system and gimbal mount, according to an aspect of the present invention.

The gimbal mount 230 mounts to the port flange on the turbomachine's casing. For example, the gimbal mount may be mounted to the port or vessel flange with the use of bolts and nuts. The leveling feet 231 may then be adjusted until they contact the vessel or casing. The gimbal mount is configured to permit radial and axial adjustment of the probe's location. When the probe 212 is inserted in the turbomachine the sensor head 213 may be too near or too far away from a blade, or it may be too near or too far away from the rotor shaft. Four turnbuckles 340 are located at 90 degree intervals around the gimbal mount. In FIG. 4, the top (i.e., 0 degree) and side (270 degree) turnbuckles are shown, and in FIG. 5 only the top (0 degree) and bottom (90 degree) turnbuckles are shown. To adjust the axial position of sensor head 213, the side (first set of) turnbuckles can be adjusted. For example, the 90 degree turnbuckle can be tightened and the 270 degree turnbuckle can be loosened to move the sensor head 213 in the axial direction. To adjust the sensor head in the tangential direction, the 0 degree and 180 degree (second set of) turnbuckles can be respectively tightened and loosened. This adjustability is extremely helpful as the port flanges are not always manufactured to close tolerances and many (if not all) were never designed to be used with highly accurate inspection equipment, such as the present invention. This adjustability also permits the operator to align the probe 212 so that the probe 212 or sensor head 213 do not contact undesired rotating parts of the turbomachine.

The gimbal mount 230 and pressure isolation system 220 may be attached to the traverse actuator system via mounting plate 350, which is attached to rail 301. The traverse actuator system includes a complementary mounting plate 302 (attached to rail 303) and the keys 351 ensure proper alignment between the traverse actuator system and the pressure isolation system/gimbal mount. The keys 351, which may be attached to either mounting plate, are interposed between the mounting plate 350 and the complementary mounting plate 302. As can be seen, the keys 351 ensure proper alignment between the traverse actuator system 210 and the pressure isolation system 220 and gimbal mount 230.

Figure 6:
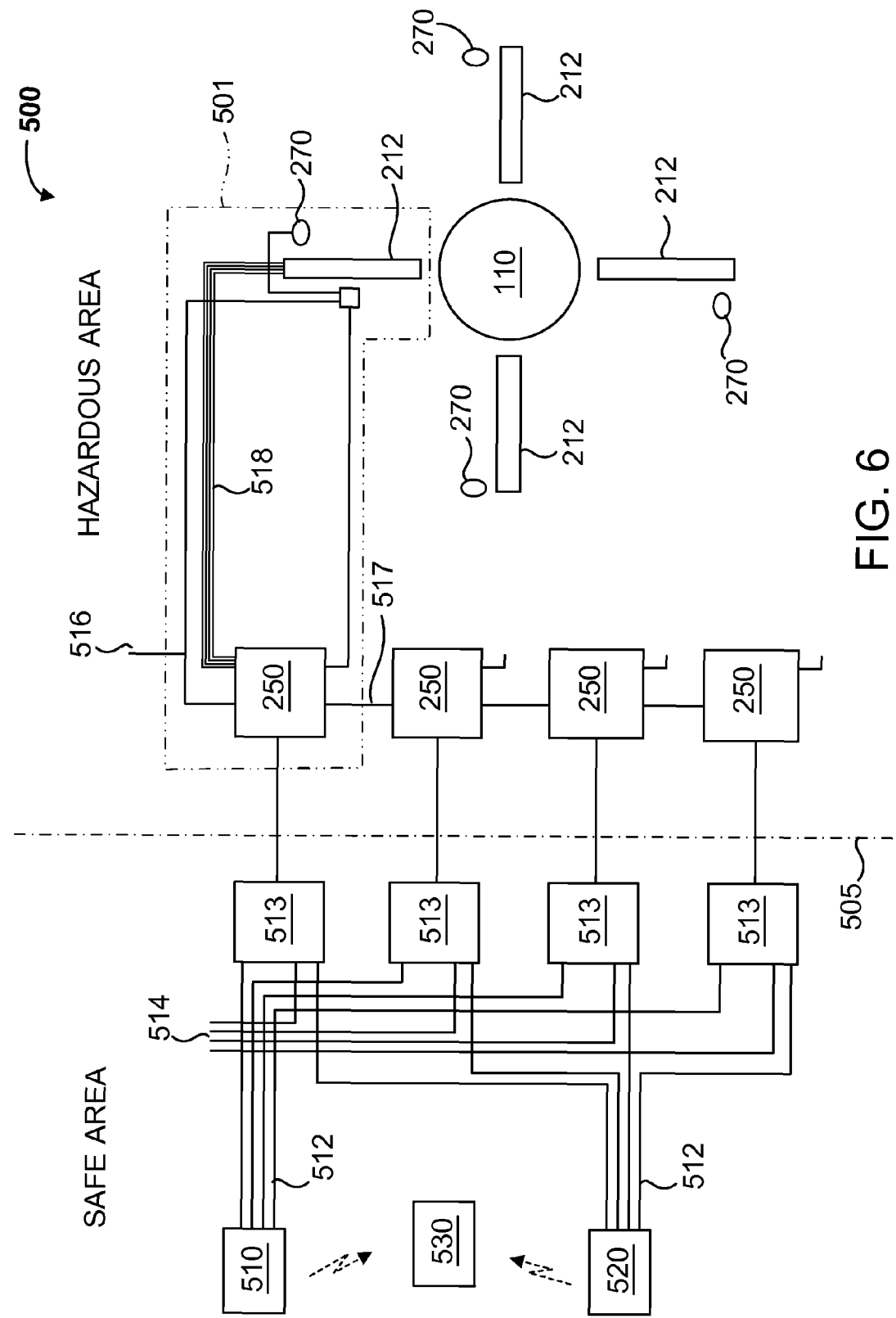
FIG. 6 illustrates a schematic diagram of a system that may be used to inspect a turbomachine, according to an aspect of the present invention.

FIG. 6 illustrates a schematic diagram of a system 500 that may be used to inspect a turbomachine, according to an aspect of the present invention. The system 500 includes the traverse actuator 210, pressure isolation system 220 and gimbal mount 230, generally indicated by 501. Four of these systems 501 are distributed around, and are attached to, the turbomachine 110. However, only the cabling and communication links are shown for one system, for clarity. Each system 501 can inspect a different part or stage of the turbomachine. The turbomachine 110 (e.g., a steam turbine) is located in a hazardous area (located to the right of line 505), and a safe area (located to the left of line 505) is located away from the steam turbine 110. The hazardous area may be the area directly around the turbomachine, or a room enclosing the turbomachine. The safe area may be located either a safe distance away from the turbomachine, in a different room or in a remote monitoring station. The system control computer 510 and camera control computer 520 are both located in the safe area. Both the system control computer 510 and the camera control computer may be connected to the enclosure 250 and monitoring station/display 530 by a wired or wireless link. For example, ethernet cables 512 may be employed as a communication link. However, any suitable wired or wireless (e.g., radio frequency, wifi, Bluetooth, etc.) communication link may be employed. In some applications, the system control computer 510 and camera control computer 520 may be combined into a single device. The system control computer 510 or the camera control computer 520 may function as a monitoring station having a display, or the monitoring station/display 530 may be a separate device or located remotely from the system 501 or system 500.

The controller 513 may also include power inputs 514 (e.g., 90-240 volts AC) for powering electrical devices, and a pressurized gas input 516 for supplying pressurized gas to the pressure seal block 320 via gas output 517. For example, pressurized air at about 60 PSI may be supplied to seal block 320 via gas output 517. A plurality of motor and feedback cables 518 extend between the controller 513 and enclosure 250. With this arrangement and configuration, a remotely located operator (in the safe area) can monitor and control the inspection process. The cameras 270 may be controlled (e.g., panned, zoomed focused, etc.) by camera control 520. The system 501 and probe 212 can be controlled with system control computer 510. The system control computer may also include a display for viewing images from cameras 270. The system control computer 510 also includes a human machine interface (HMI) for controlling the probe 212. For example, linear (i.e., radial) movement of the probe is controlled as well as activation of motor 260, and rotation (i.e., yawing) of the probe 212 by yaw drive 216 is controlled. The system control computer 510 may also display PSI readings, warnings/alarms, temperatures, and any other data that may be of interest during the inspection and/or testing process.

Figure 7:
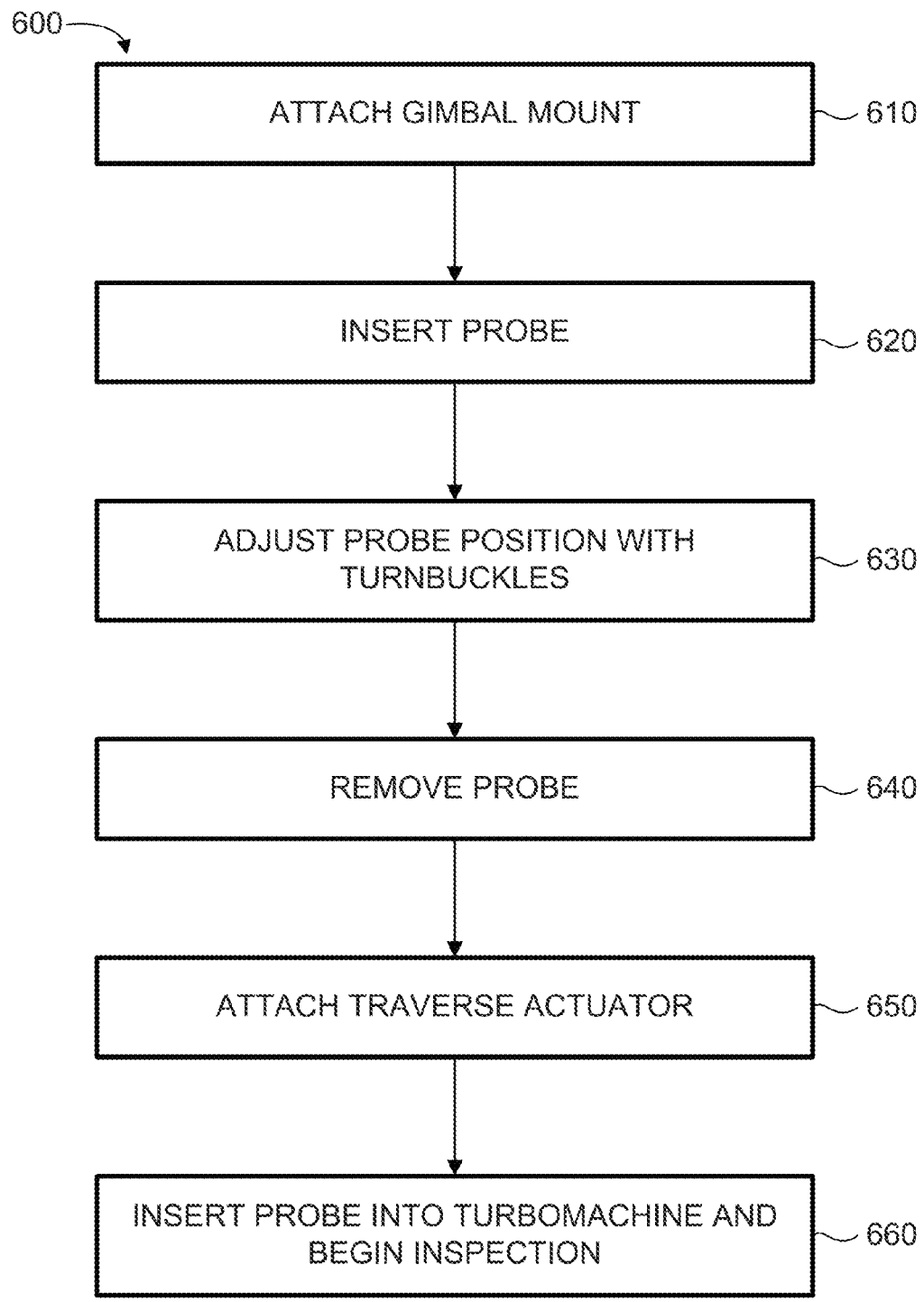
FIG. 7 illustrates a flowchart of a method for inspecting a turbomachine, according to an aspect of the present invention.

FIG. 7 illustrates a flowchart of a method 600 for inspecting a turbomachine, according to an aspect of the present invention In step 610, the gimbal mount 230 is attached to the vessel flange of the turbomachine with mechanical fasteners. The leveling feet 231 are adjusted until they contact the vessel (the vessel is the turbomachine casing), and may be locked in place with lock nuts. In step 620, a probe or camera may be inserted into the turbomachine through the gimbal mount. In step 630, the position of the probe is adjusted with the gimbal mount's turnbuckles 340. Once the desired probe position and orientation is obtained the turnbuckles may be locked in place with jam nuts. In step 640, the probe may be removed from the turbomachine and gimbal mount 230. In step 650, the traverse actuator 210 is attached to the gimbal mount 230 and pressure isolation system 220 via mounting plates 350, 302. The alignment keys 351 ensure correct probe alignment between the pressure isolation system and the traverse actuator. Mechanical fasteners may be used to attach the traverse actuator to the mounting plate 350. The traverse actuator system is also connected to the gimbal mount through or via the pressure isolation system. The leg assembly may now be deployed and adjusted to the desired height. The legs of the leg assembly may be telescoping to allow for easy height adjustment. In step 660, the probe 212 is re-inserted into the turbomachine through the pressure isolation system and gimbal mount. In step 670, the system is activated to insert the probe into the machine to begin the inspection and/or testing and take readings of various parameters (e.g., pressure, temperature, moisture, etc.).

Figure 8:
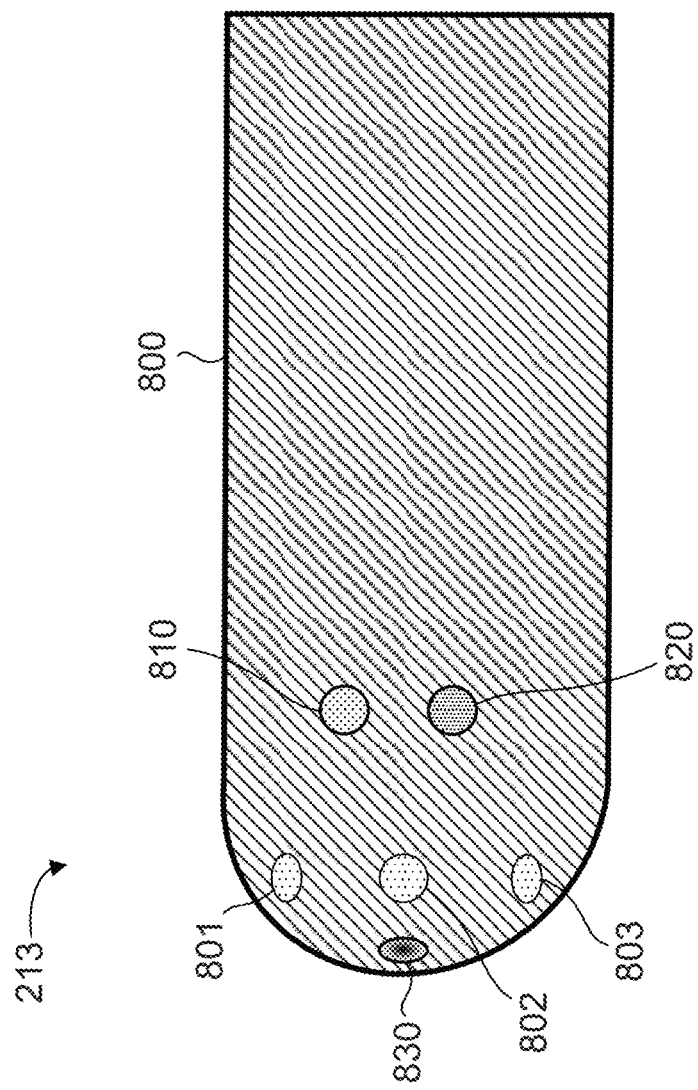
FIG. 8 illustrates a partial side view of the sensor head, according to an aspect of the present invention.

FIG. 8 illustrates a partial side view of the sensor head 213, according to an aspect of the present invention. The sensor head 213 may comprise a pressure probe 800 that has a plurality of ports 801-803. The ports 801-803 may be pressure sensing ports and the sensor head may include one to seven or more pressure sensing ports. Multiple ports allow for differential pressure sensing capabilities, and the multiple ports may be evenly or unevenly distributed around the distal end of probe 800. For example, the pressure at a specific location (e.g., between specific stages, or at specific radial or axial locations) in the turbomachine may be desired and the probe 800 can detect this pressure. The probe 800 may also include a moisture probe/port 810 and a temperature probe/port 820. Alternatively, the entire probe 800 may be configured as a moisture or temperature probe. The probe 800 may also include a camera 830 or imaging device. For example, the camera 830 can aid in verifying accurate probe placement or in identification of foreign objects/debris or damage.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for inspecting a turbomachine, the method comprising the steps of:
   attaching a gimbal mount to the turbomachine;
   inserting a probe into the turbomachine through the gimbal mount;
   adjusting a position of the probe via the gimbal mount;
   removing the probe from the turbomachine;
   attaching a traverse actuator system to the gimbal mount, the gimbal mount comprising a plurality of turnbuckles located at equal intervals around the gimbal mount, and wherein the gimbal mount is configured to be mounted to a port or a vessel flange of the turbomachine, and adjustment of the turnbuckles translates into a tangential or axial adjustment of a sensor head position for the probe, the traverse actuator system is connected to the gimbal mount through a pressure isolation system;
   reinserting the probe back into the turbomachine; and
   inspecting or testing the turbomachine.

2. The method of claim 1, wherein there are four turnbuckles located at 90 degree intervals around the gimbal mount, the adjusting a position of the probe step further comprising:
   adjusting a first set of turnbuckles spaced by 180 degrees to move the probe in an axial direction with respect to the turbomachine, and adjusting a second set of turnbuckles spaced by 180 degrees to move the probe in a tangential direction with respect to the turbomachine;
   wherein the first set of turnbuckles is 90 degrees offset from the second set of turnbuckles.

3. The method of claim 1, the attaching a traverse actuator system step further comprising:
   connecting a mounting plate to a complementary mounting plate, the mounting plate is attached to a rail, and the rail supports both the pressure isolation system and the gimbal mount, the mounting plate is configured to align with the complementary mounting plate connected to the traverse actuator system; and
   wherein a plurality of keys are interposed between the mounting plate and the complementary mounting plate to ensure alignment between the traverse actuator system and the gimbal mount.

4. The method of claim 1, wherein the inspecting step further comprises:
   reading at least one of pressure values, temperature values or moisture values obtained from within the turbomachine.

5. The method of claim 1, the probe further comprising at least one of:
   a pressure probe having a plurality of ports, a moisture probe, a temperature probe, a camera.

6. The method of claim 1, the probe further comprising:
   a pressure probe having a plurality of ports, and an elongated shaft having a sensor head located at one end and a plurality of output ports located at an opposing end of the elongated shaft.

7. The method of claim 1, the pressure isolation system further comprising:
   a valve seal located between the gimbal mount and a pressure seal, the valve seal configured to isolate the pressure seal from the gimbal mount when the probe is not in the valve seal; and
   a probe bearing located adjacent to the pressure seal, the probe bearing configured to facilitate back and forth movement of the probe by reducing friction.

8. The method of claim 7, wherein the valve seal is at least one of:
   a ball valve seal or a guillotine seal.

9. The method of claim 7, wherein the probe bearing is comprised of at least one of:
   roller bearings, ball bearings, or low friction material.

10. The method of claim 7, further comprising the step of:
    connecting the pressure seal to a pressurized source or a vacuum source.

11. The method of claim 1, the traverse actuator system further comprising:
    a carriage configured to move the probe into and out of the turbomachine;

a track having a plurality of linearly arranged teeth, the track configured for operation with the carriage; and a motor operably connected with the carriage and track, the motor configured to engage the plurality of linearly arranged teeth so that operation of the motor forces the carriage to move along the track.

12. The method of claim 11, the traverse actuator system further comprising:

an enclosure configured to operate in hazardous environments, the enclosure housing the motor; and a yaw drive configured to rotate the probe about a radial axis of the turbomachine.

13. The method of claim 11, the traverse actuator system further comprising:

monitoring an insertion location of the probe with a camera, the camera configured to operate in hazardous environments; and wherein the camera is connected to a monitoring station having a display.

14. The method of claim 11, the traverse actuator system further comprising:

a leg assembly attached to a rail of the traverse actuator system, the leg assembly configured to stabilize the traverse actuator system, the leg assembly having a plurality of adjustable length legs configured to lock in position at a desired length.

15. The method of claim 11, the traverse actuator system further comprising:

an articulated cable guide comprised of a plurality of chain links, the articulated cable guide configured to retain a plurality of cables, and to follow movement of the carriage so that the cables avoid catching on obstructions.

16. A method for inspecting an operating turbomachine, the method comprising the steps of:

attaching a gimbal mount to the turbomachine, the gimbal mount comprising a plurality of turnbuckles located at equal intervals around the gimbal mount, and wherein the gimbal mount is configured to be mounted to a port or a vessel flange of the turbomachine, and adjustment of the turnbuckles translates into a tangential or axial adjustment of a sensor head position for a probe;

inserting the probe into the turbomachine through the gimbal mount;

adjusting a position of the probe via the gimbal mount;

removing the probe from the turbomachine;

attaching a traverse actuator system to the gimbal mount, the traverse actuator system is connected to the gimbal mount through a pressure isolation system, connecting a mounting plate to a complementary mounting plate, the mounting plate is attached to a rail, and the rail supports both the pressure isolation system and the gimbal mount, the mounting plate is configured to align with the complementary mounting plate connected to the traverse actuator system, a plurality of keys are interposed between the mounting plate and the complementary mounting plate to ensure alignment between the traverse actuator system and the gimbal mount;

reinserting the probe back into the turbomachine; and inspecting or testing the turbomachine, and reading at least one of pressure values, temperature values or moisture values obtained from within the operating turbomachine.

17. The method of claim 16, the probe further comprising at least one of:

a pressure probe having a plurality of ports, a moisture probe, a temperature probe, a camera, or an elongated shaft having a sensor head located at one end and a plurality of output ports located at an opposing end of the elongated shaft.

18. The method of claim 17, the pressure isolation system further comprising:

a valve seal located between the gimbal mount and a pressure seal, the valve seal configured to isolate the pressure seal from the gimbal mount when the probe is not in the valve seal; and a probe bearing located adjacent to the pressure seal, the probe bearing configured to facilitate back and forth movement of the probe by reducing friction, the probe bearing comprised of at least one of, roller bearings, ball bearings, or low friction material.

19. The method of claim 18, the traverse actuator system further comprising:

a carriage configured to move the probe into and out of the turbomachine;

a track having a plurality of linearly arranged teeth, the track configured for operation with the carriage;

a motor operably connected with the carriage and track, the motor configured to engage the plurality of linearly arranged teeth so that operation of the motor forces the carriage to move along the track;

an enclosure configured to operate in hazardous environments, the enclosure housing the motor;

a yaw drive configured to rotate the probe about a radial axis of the turbomachine; and an articulated cable guide comprised of a plurality of chain links, the articulated cable guide configured to retain a plurality of cables, and to follow movement of the carriage so that the cables avoid catching on obstructions.

20. A method for inspecting a turbomachine, the method comprising the steps of:

attaching a gimbal mount to the turbomachine;

inserting a probe into the turbomachine through the gimbal mount;

adjusting a position of the probe via the gimbal mount;

removing the probe from the turbomachine;

attaching a traverse actuator system to the gimbal mount, the traverse actuator system is connected to the gimbal mount through a pressure isolation system, the pressure isolation system comprising a valve seal located between the gimbal mount and a pressure seal, the valve seal configured to isolate the pressure seal from the gimbal mount when the probe is not in the valve seal, and a probe bearing located adjacent to the pressure seal, the probe bearing configured to facilitate back and forth movement of the probe by reducing friction, wherein the valve seal is at least one of a ball valve seal or a guillotine seal;

reinserting the probe back into the turbomachine; and inspecting or testing the turbomachine.

21. The method of claim 20, wherein there are four turnbuckles located at 90 degree intervals around the gimbal mount, the adjusting a position of the probe step further comprising:

adjusting a first set of turnbuckles spaced by 180 degrees to move the probe in an axial direction with respect to the turbomachine, and adjusting a second set of turnbuckles spaced by 180 degrees to move the probe in a tangential direction with respect to the turbomachine; wherein the first set of turnbuckles is 90 degrees offset from the second set of turnbuckles.

22. The method of claim 20, the attaching a traverse actuator system step further comprising:

connecting a mounting plate to a complementary mounting plate, the mounting plate is attached to a rail, and the rail supports both the pressure isolation system and the gimbal mount, the mounting plate is configured to align with the complementary mounting plate connected to the traverse actuator system; and wherein a plurality of keys are interposed between the mounting plate and the complementary mounting plate to ensure alignment between the traverse actuator system and the gimbal mount.

23. The method of claim 20, wherein the inspecting step further comprises:

reading at least one of pressure values, temperature values or moisture values obtained from within the turbomachine.

24. The method of claim 20, the probe further comprising at least one of:

a pressure probe having a plurality of ports, a moisture probe, a temperature probe, a camera.

25. The method of claim 20, the probe further comprising:

a pressure probe having a plurality of ports, and an elongated shaft having a sensor head located at one end and a plurality of output ports located at an opposing end of the elongated shaft.

26. The method of claim 20, wherein the probe bearing is comprised of at least one of:

roller bearings, ball bearings, or low friction material.

27. The method of claim 20, further comprising the step of:

connecting the pressure seal to a pressurized source or a vacuum source.

28. The method of claim 20, the traverse actuator system further comprising:

a carriage configured to move the probe into and out of the turbomachine;

a track having a plurality of linearly arranged teeth, the track configured for operation with the carriage; and a motor operably connected with the carriage and track, the motor configured to engage the plurality of linearly arranged teeth so that operation of the motor forces the carriage to move along the track.

29. The method of claim 28, the traverse actuator system further comprising:

an enclosure configured to operate in hazardous environments, the enclosure housing the motor; and a yaw drive configured to rotate the probe about a radial axis of the turbomachine.

30. The method of claim 28, the traverse actuator system further comprising:

monitoring an insertion location of the probe with a camera, the camera configured to operate in hazardous environments; and wherein the camera is connected to a monitoring station having a display.

31. The method of claim 28, the traverse actuator system further comprising:

a leg assembly attached to a rail of the traverse actuator system, the leg assembly configured to stabilize the traverse actuator system, the leg assembly having a plurality of adjustable length legs configured to lock in position at a desired length.

32. The method of claim 28, the traverse actuator system further comprising:

an articulated cable guide comprised of a plurality of chain links, the articulated cable guide configured to retain a plurality of cables, and to follow movement of the carriage so that the cables avoid catching on obstructions.

* * * * *